(12) United States Patent
Casati et al.

(10) Patent No.: US 6,370,947 B1
(45) Date of Patent: Apr. 16, 2002

(54) SUBSTRATE SURFACE ANALYSIS

(75) Inventors: Donato Casati, Merate; Fabio Mauri, Bernareggio, both of (IT)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 09/382,890

(22) Filed: Aug. 25, 1999

(30) Foreign Application Priority Data

Sep. 8, 1998 (GB) ............................................. 9819533

(51) Int. Cl.[7] ............................................. G01N 13/00
(52) U.S. Cl. ........................................ 73/64.52; 73/73
(58) Field of Search ...................... 73/64.48, 64.52, 73/73, 104

(56) References Cited

U.S. PATENT DOCUMENTS

| | | | |
|---|---|---|---|
| 2,819,611 A | * 1/1958 | Shellard et al. | 73/64 |
| 3,733,893 A | * 5/1973 | Bickford et al. | 73/73 |
| 4,050,822 A | 9/1977 | Grat | |
| 4,438,500 A | * 3/1984 | Collins et al. | 364/567 |
| 4,475,666 A | * 10/1984 | Bilbrey et al. | 222/14 |
| 4,712,627 A | * 12/1987 | Harrington et al. | 177/50 |
| 5,268,733 A | 12/1993 | Wright et al. | |
| 5,538,717 A | * 7/1996 | La Poterie | 424/61 |
| 5,583,285 A | * 12/1996 | Hahn et al. | 73/64.52 |
| 5,990,013 A | * 11/1999 | Berenguer et al. | 438/706 |

* cited by examiner

Primary Examiner—Hezron Williams
Assistant Examiner—Charles D. Garber
(74) Attorney, Agent, or Firm—Schmeiser, Olsen & Watts; Lawrence R. Fraley

(57) ABSTRACT

A method and apparatus for estimating the degree of cleanliness of a substrate surface by measuring the surface wettability, particularly of an inorganic surface used in the manufacturing of electronic components. The wettability of the substrate surface is measured by depositing a droplet of test liquid on the substrate surface and measuring the speed at which the droplet evaporates. This speed is proportional to the droplet liquid surface area, which depends on the substrate surface wettability. A good surface wettability indicates a clean surface.

18 Claims, 2 Drawing Sheets

SUBSTRATE SURFACE ANALYSIS

TECHNICAL FIELD

The present invention relates to a method and apparatus for analyzing the characteristics of substrate surfaces.

BACKGROUND OF THE INVENTION

In the manufacturing process of an electronic package, many operations require a cleaning step. However, even the most accurate cleaning method can leave some contamination. Many circumstances require that the cleanliness of a surface be tested and measured to verify that the contamination of the part is contained within acceptable limits. Furthermore, a check on the cleanliness of a surface may be required when a part is moved between processing steps where handling or transportation is required. For example a cleaning step or a check of the cleanliness degree may be required before electroplating a part, or before a component is soldered onto a plated pad. An example is the mounting of a chip (device) on a substrate, usually done through soldering: this is called "first level packaging". This stage of the process needs to be performed in a "clean" environment to avoid contamination of the parts, before the module is encapsulated, usually with a resin, and the circuits are protected by external agents.

The meaning of "clean" can vary significantly according to the application field considered. In precision cleaning applications, in which the required degree of cleanliness is very high, such as in the manufacture of medical components or electronic products, an accurate assessment of surface cleanliness is needed in order to meet the expected quality parameters. An accurate cleanliness assessment also helps in protecting the environment against pollution from cleaning agents, by evaluating new cleaning methods or optimizing the existing cleaning processes.

In the manufacturing of electronic components and products, the contamination of a surface can be caused by a number of different factors. Examples of contamination are: deposition of small particles; ionic contamination; deposition of chemical compound layers (e.g., oils or salts) occurring during manufacturing steps; adsorption of organic material (e.g., hydrocarbons or moisture) caused by exposure to the atmosphere.

Methods for measuring the degree of cleanliness can be divided into two categories: a) direct methods; and, b) indirect methods. Direct methods analyze the surface to be checked to discover whether the contamination of the surface exceeds a predetermined threshold. These methods either are dependent on human discretion, such as in a magnified visual inspection, or require sophisticated and very expensive equipment. Indirect methods are based on the analysis of a very powerful solvent after it has been used to extract the contaminants from a specimen surface.

One direct method is the so called "angle of contact" method. The angle of contact method is based on the measurement of the surface wettability. The contact angle is the angle between the substrate surface and the tangent of a liquid droplet deposited on the substrate, at the point of contact of the liquid droplet with the substrate surface. This contact angle depends on the surface wettability. An ideal, perfect wettability would cause the droplet to spread out over the substrate, giving a contact angle approaching 0°. A good wettability value would indicate a clean surface, while a bad wettability value is a symptom of contamination of the surface. For example, with inorganic surfaces, the surface wettability is affected by surface organic contamination. By detecting any displacement on the wettability value from the expected one, an accurate estimate of the degree of cleanliness can be derived.

It is known to measure this contact angle by projecting a profile image of the deposited droplet on a screen and estimating the contact angle by measurement on the projected image. One problem with this method is that the measurement of the angle is subject to significant errors and it is unreliable because of human intervention.

U.S. Pat. No. 4,050,822 describes a method for determining the wettability of a material by measuring the height of a drop of a liquid deposited on its surface and comparing the height measurements to standard drop measurements. This method is subject to visual human error in coincident comparison of a drop with a graduated scale and requires an elaborate optical system.

U.S. Pat. No. 5,268,733 describes a method for determining the contact angle by measuring, on a projected image of the droplet, the angle between a base line defined by the substrate surface and a reference line, which connects the contact point of the droplet with the substrate and an apex point of the droplet. This method provides a more reliable measurement of the contact angle, but still suffers from the difficulty of obtaining the measurement and of the human intervention in the determination of the angle.

Another drawback of the "angle of contact" method is that it is applicable only to flat, smooth surfaces, otherwise, irregularities of the surface would affect the tangent angle measurement.

For the above reasons a more accurate and reliable method would be highly desirable for the detection of contamination (e.g., organic) on a substrate (e.g., inorganic) surface. It is an object of the present invention to provide a technique which overcomes the above drawbacks.

OBJECTS AND SUMMARY OF THE INVENTION

An object of the present invention is to provide a method for measuring the degree of cleanliness of a substrate surface.

A more specific object of the present invention is to provide such a method adapted for measuring organic contamination on the surface of an inorganic substrate.

Yet another object of the present invention is to provide an apparatus to measure the degree of cleanliness of a substrate surface by depositing a droplet of liquid on a substrate surface and determining the rate of evaporation of the droplet of liquid.

A further object of the present invention is to provide a method to measure the degree of cleanliness of a substrate surface by providing a ratio of the evaporation rate of a droplet of liquid on a substrate surface, and the expected evaporation rate of a drop of liquid on a clean substrate surface.

According to one aspect of the present invention, there is provided a method for analyzing the characteristics of a substrate surface, comprising the steps of depositing a droplet of liquid on a substrate surface, and determining a measure indicative of the evaporation rate of the droplet of liquid, which is indicative of the liquid surface area of the droplet of liquid.

According to another aspect of the invention, there is provided an apparatus for revealing contamination and measuring the cleanliness of a substrate surface comprising a support structure for holding a substrate having a surface, a depositing member for depositing a liquid droplet of a predetermined volume on the surface of the substrate, a measuring structure for measuring the time $T_e$ taken by the liquid droplet to lose a predetermined percentage of its weight, and a comparing structure for comparing the measured time $T_e$ with an expected value for a clean substrate surface.

BRIEF DESCRIPTION OF THE DRAWINGS

Various embodiments of the invention will now be described in detail by way of examples, with reference to accompanying figures, where.

DETAILED DESCRIPTION OF THE PREFERRED EMBODIMENT

For a better understanding of the present invention, together with other and further objects, advantages and capabilities thereof, reference is made to the following disclosure and appended claims in connection with the above-described drawings.

Figure 1:
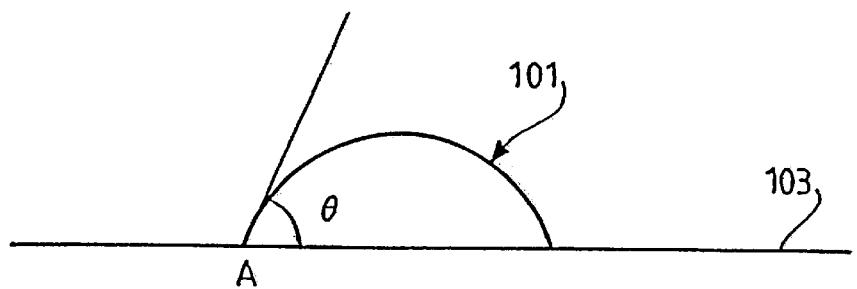
FIG. 1 shows schematically the angle of contact between a droplet of liquid and a surface.

The wettability of a surface can be expressed as the contact angle of a droplet of liquid deposited on a substrate surface. The contact angle is the angle between the imaginary base line defined by the substrate surface and the tangent to the droplet at the point of contact between the droplet and the substrate surface. With reference to FIG. 1, the angle of contact is represented. Considering a liquid sessile droplet 101 on a solid surface 103, the contact angle is defined as the angle θ between the surface line and the tangent to the curve (droplet profile) at the contact point A. The wettability and its quantitative measurement can be used as a surface analysis technique in several applications, i.e., evaluation of surface cleanliness, surface treatments, surface energy. The bigger the contact angle the lower the wettability of the surface, because with an ideal completely "wettable" surface, the droplet should theoretically spread out over the surface and the contact angle would approach 0°.

Figure 2:
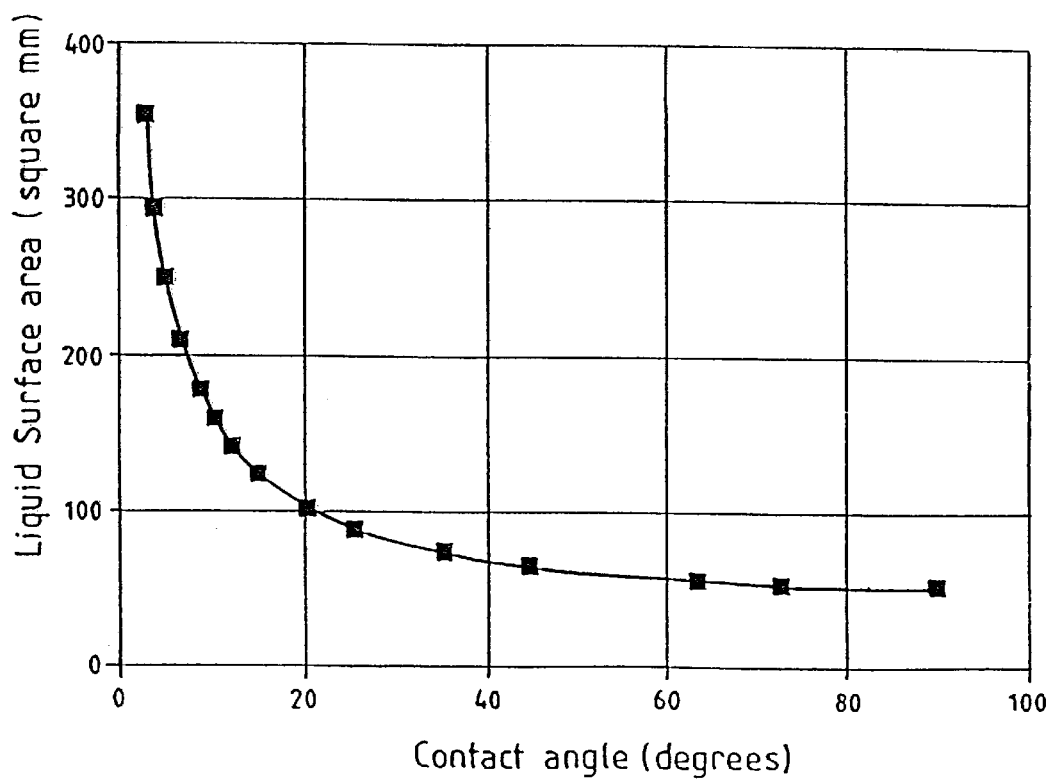
FIG. 2 shows the relationship existing between the angle of contact of a droplet of liquid on a surface and the droplet of liquid surface area.

Another way of representing the wettability of a surface is through the liquid surface area, i.e., the free surface area of the droplet, when the droplet is deposited on the surface. FIG. 2 represents the relationship which exists between the contact angle of a droplet, as defined above, and the liquid surface area. The graph of FIG. 2 relates to a droplet having a volume of 50 μl and it clearly shows that with small contact angles the liquid surface area of the droplet is large, while with wider contact angles (i.e., with poor surface wettability) the liquid surface area decreases and tends to an asymptote. Thus, knowing the liquid surface area of a droplet would give precise indication of the wettability of a surface. The liquid surface area itself is not easy to measure, but there is a direct and linear relationship between the liquid surface area and the speed at which the liquid droplet evaporates.

According to a preferred embodiment of the present invention the liquid surface area of a droplet on a substrate surface is determined by measuring the speed at which a droplet of a predetermined size in a predetermined environment, loses weight from evaporation.

Figure 3:
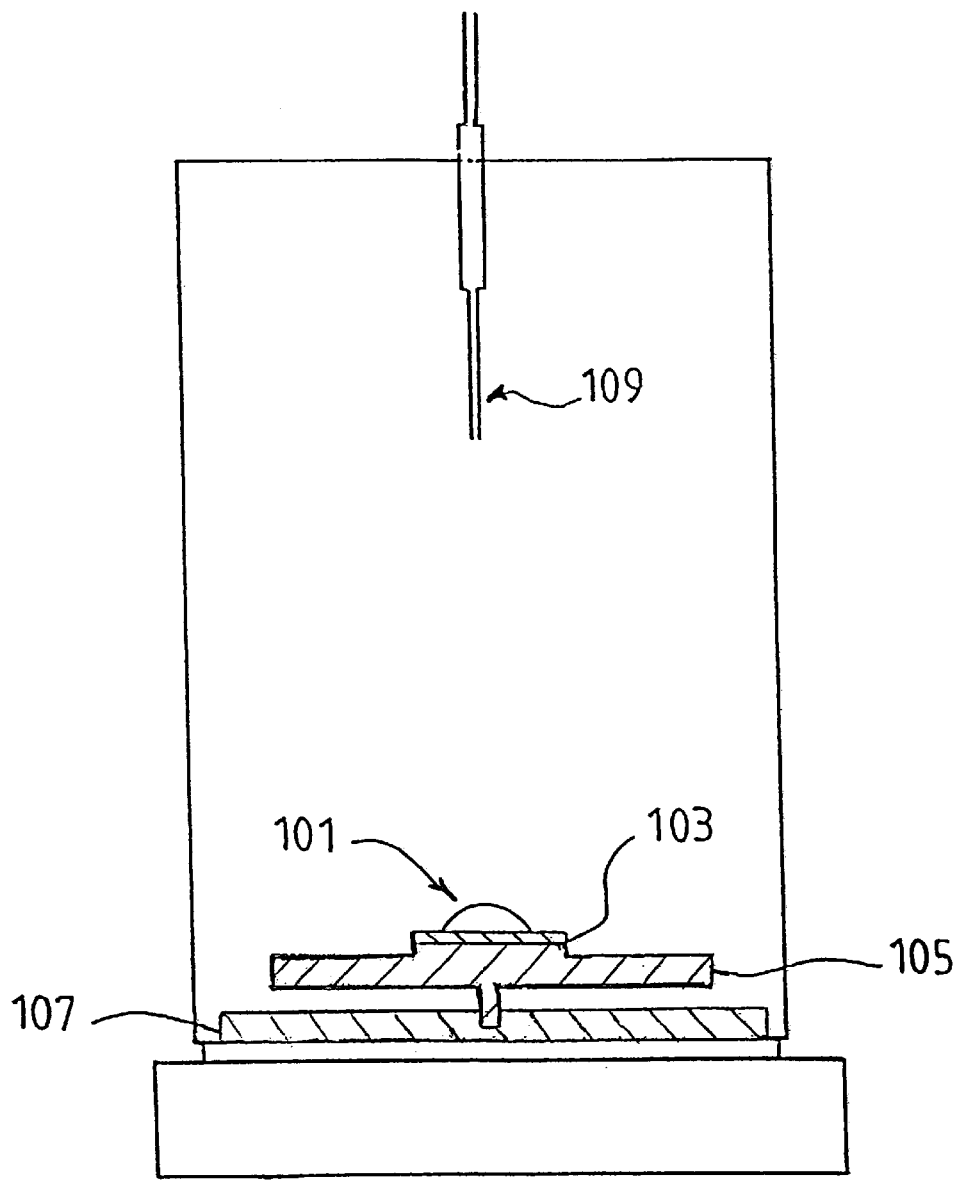
FIG. 3 shows schematically the measurement apparatus according to a preferred embodiment of the present invention.

FIG. 3 is a schematic representation of the wettability measuring apparatus according to a preferred embodiment of the present invention. An electronic balance 107 has a balance plate 105 which carries the surface 103 to be analyzed. Several commercially available precision balances may be used; for example, an electronic balance produced by Mettler-Toledo Inc., Columbus, Ohio. According to a preferred embodiment of the present invention, the balance should be able to record weights to the nearest 0.1 mg. A syringe 109 comes close to the plate 105 to gently deposit a liquid droplet 101 of a predetermined size. In a preferred embodiment of the present invention the droplet volume is 50 μl; the liquid used, for example, is deionized water (DI water). Other liquids may be used according to the expected contamination of the surface to be tested. According to a preferred embodiment of the present invention DI water is used when hydrophobic contaminants (e.g., oils, grease, silicones) are expected to be detected on the surface. In case hydrophilic contaminants are suspected, a non-polar liquid (e.g., diiodomethane or α-bromonaphtalene) may be preferred. The reason is that the combination of water with hydrophilic materials may give unreliable results. A microprocessor CPU (e.g., a personal computer), not shown, controls all the operations and records the results. According to a preferred embodiment of the present invention, the time taken by the droplet to lose a predetermined portion of weight (e.g., 20%) under predetermined environmental conditions is recorded by a CPU. The ratio between the weight loss Δm and the time taken Δt is the initial evaporating rate, which is proportional to the liquid surface area: the wider the surface area, the faster is the evaporation. According to a preferred embodiment of the present invention, the weight loss is fixed, so the liquid surface area can be estimated in relation (inversely proportional) to the time Δt.

As mentioned above, the surface wettability can give useful indications of the cleanliness of the surface, e.g., a metal or ceramic surface in the manufacture of microelectronic components. If an inorganic surface has organic contamination present, the wettability values are significantly affected. The recorded results can be compared with expected values of an ideally clean surface or even normalized into a more easily readable scale to have an immediate representation of the surface cleanliness. According to a preferred embodiment of the present invention the cleanliness of the tested surface is determined by comparing the measured time $T_e$ with reference values expected for a clean surface.

While there have been shown and described what are at present considered the preferred embodiments of the invention, it will be obvious to those skilled in the art that various modifications can be made therein without departing from the scope of the invention as defined by the appended claims.

What is claimed is:

1. A method for analyzing the characteristics of a substrate surface, comprising the steps of:

depositing a droplet of liquid on a substrate surface; and, determining a measure indicative of the evaporation rate of said droplet of liquid, which is indicative of the liquid surface area of said droplet of liquid, by measuring the time $T_e$ taken by the droplet of liquid to lose a predetermined portion of its weight by evaporation.

2. The method of claim 1 wherein said droplet of liquid deposited on said substrate surface has a predetermined volume.

3. The method of claim 2 further including the step of comparing said time $T_e$ with an expected value for a clean substrate surface.

4. The method of claim 1 further including the step of determining the surface wettability based on said surface area of said droplet of liquid.

5. The method of claim 1 further including the step of comparing said measure indicative of said evaporation rate of said droplet of liquid on said substrate surface with an expected value for a clean substrate surface.

6. The method of claim 1 further including the step of determining the angle of contact of said droplet of liquid on said substrate surface, based on said surface area of said droplet of liquid.

7. The method of claim 1 wherein said substrate surface is inorganic.

8. The method of claim 1 wherein said droplet of liquid is deionized water.

9. The method of claim 1 wherein said droplet of liquid is a non-polar liquid.

10. An apparatus for revealing contamination and measuring the cleanliness of a substrate surface, comprising:
 a support structure for holding a substrate having a surface;
 a depositing member for depositing a liquid droplet of a predetermined volume on said surface of said substrate;
 a measuring structure for measuring the time $T_e$ taken by said liquid droplet to lose a predetermined portion of its weight; and,
 a comparing structure for comparing said measured time $T_e$ with an expected value for a clean substrate surface.

11. The apparatus of claim 10 wherein said support structure comprises a balance plate.

12. The apparatus of claim 11 wherein said depositing member comprises a syringe.

13. The apparatus of claim 12, wherein said measuring structure comprises an electronic balance.

14. The apparatus of claim 13 wherein said comparing structure comprises a CPU.

15. The apparatus of claim 10 further including a control member for controlling said measuring structure and said comparing structure.

16. The apparatus of claim 15 wherein said control member is a microprocessor CPU.

17. The apparatus of claim 10 further including a control member for controlling said depositing member.

18. The apparatus of claim 17 herein said control member is a microprocessor CPU.

* * * * *